United States Patent [19]

Eichel et al.

[11] Patent Number: 5,238,686
[45] Date of Patent: Aug. 24, 1993

[54] SUSTAINED-RELEASE PHARMACEUTICAL PREPARATION

[75] Inventors: Herman J. Eichel; Brent D. Massmann, both of Columbus, Ohio

[73] Assignee: Kinaform Technology, Inc., Dayton, Ohio

[21] Appl. No.: 573,241

[22] Filed: Aug. 27, 1990

Related U.S. Application Data

[63] Continuation of Ser. No. 17,988, Feb. 24, 1987, abandoned, which is a continuation-in-part of Ser. No. 844,676, Mar. 27, 1986, abandoned.

[51] Int. Cl.$^5$ .......................... A61K 9/62; B01J 13/22
[52] U.S. Cl. ..................................... 424/461; 424/463; 424/494; 424/495; 428/402.24; 514/963
[58] Field of Search ................... 428/402.24; 424/461, 424/463, 495, 494; 514/963

[56] References Cited

U.S. PATENT DOCUMENTS

| | | | |
|---|---|---|---|
| 3,242,051 | 3/1966 | Hiestand et al. | 428/402.24 X |
| 3,882,228 | 5/1975 | Boncey et al. | 424/489 |
| 4,443,497 | 4/1984 | Samejima et al. | 424/495 X |
| 4,780,318 | 10/1988 | Appelgren et al. | 514/965 X |

Primary Examiner—Richard D. Lovering
Attorney, Agent, or Firm—Killworth, Gottman, Hagan & Schaeff

[57] ABSTRACT

A sustained-release pharmaceutical preparation comprising an admixture of uncoated and/or single walled water soluble drug, such as aspirin, and dual walled coated drug. The dual wall structure has an inner wall microencapsular control coating, such as ethyl cellulose, and an outer wall enteric coating such as cellulose acetate phthalate. The dual walled coated drug has a delayed, gradual, long-term release which takes place in the intestines while the uncoated and/or single walled drug has immediate therapeutic properties upon dissolution in the stomach. The outer wall enteric coating may be applied to microencapsulated core drug by a coacervation, spray coating or other process.

6 Claims, No Drawings

SUSTAINED-RELEASE PHARMACEUTICAL PREPARATION

CROSS-REFERENCE TO RELATED APPLICATION

This application is a continuation of U.S. application Ser. No. 017/988, filed Feb. 24, 1987, now abandoned, which in turn is a continuation-in-part of U.S. application Ser. No. 844,676, filed Mar. 27, 1986 now abandoned, the specification of which is hereby incorporated by reference.

BACKGROUND OF THE INVENTION

The present invention relates to sustained-release pharmaceutical preparations and the method for making them. More particularly, it relates to a granular, water-soluble drug, such as aspirin, coated with a dual wall structure to give a delayed and sustained drug delivery. The dual walled coated drug may be mixed with uncoated drug and/or single walled coated drug to provide an improved sustained-release system.

As is well known, the maximum time of effectiveness in many pharmaceutical preparations, particularly those containing a water soluble drug such as aspirin, is only a few hours because of biological modification and/or elimination of the medication in the body. Consequently, repeated dosages must be taken at frequent intervals to obtain long term pain relief. Furthermore, aspirin usually dissolves readily in the gastric juices of the stomach and the total dosage is immediately fed into the blood stream. The level of aspirin in the blood stream constantly decreases because of the biological elimination, so there is little or no pain relief at the end of the period between dosages. As a result, the pain relief fluctuates between dosages corresponding to the peaks and valleys in the level of aspirin in the blood.

Many attempts have been made to develop timed-released pharmaceutical preparations which provide a more constant level of the drug in the blood over several hours.

One common approach is to microencapsulate aspirin, for example, with a capsule wall material which provides a slower dissolution rate than free aspirin. The early work in that regard is represented by U.S. Pat. Nos. 3,155,590; 3,341,416; 3,488,418, and 3,531,418. Those patents, among others, disclose dispersing particles of aspirin in a hot cyclohexane solution containing ethyl cellulose and then introducing a phase-separation inducing agent, such as butyl rubber or polyethylene. Upon cooling, the aspirin particles become coated with ethyl cellulose. The coated particles are then admixed with tabletting excipients and formed into dosage-sized tablets. When ingested, the tablets disintegrate rapidly and the individual particles of encapsulated aspirin are dispersed in the stomach. The gastric juices slowly diffuse through the capsule walls, dissolve the aspirin, and the dissolved aspirin slowly diffuses or leaches out through the capsule walls into the body. Although the resultant blood level content is sustained to a measurable extent, the aspirin is diffused into the body rapidly enough so there is an initially high bllod level content which decreases quite rapidly within a few hours. These dissolution properties yield undesirable blood aspirin concentration versus time curves.

In the first place, the time required to reach therapeutic levels after ingestion is longer for timed-release aspirin than for free aspirin. For this reason, it has been proposed that free aspirin be tableted with coated aspirin particles,. See, for example, U.S. Pat. No. 3,115,441 which discloses mixing aspirin particles having a series of coatings thereon with uncoated aspirin, and tableting so that the coated particles are entrapped in uncoated aspirin. Tablets made according to the method have the advantage of providing immediate relief because the free aspirin (which comprises the initial dosage) dissolves immediately upon ingestion. However, as with the other preparations discussed above, the tablet rapidly disintegrates in the stomach.

See also Guy U.S. Pat. No. 4,025,613 where a multilayered tablet is disclosed. One layer comprises aspirin coated with cellulose acetate phthalate and the other layer is free aspirin. However, as stated in Dunn, U.S. Pat. No. 4,520,009, while aspirin tablets prepared by the process of Guy exhibit desirable in vitro release properties, processing difficulties are encountered in production runs. Dunn, then, is said to be an improvement in that large batch processing is allegedly made easier. In Dunn an admixture of aspirin, microcrystalline cellulose, cellulose acetate phthalate, plasticizer, corn starch and lubricant is compressed into tablet form. There is no microencapsulation as such in Dunn and, accordingly, the advantages of microencapsulated particles are foregone in favor of processing ease.

With microencapsulated particles, as discussed above, the dissolution rate decreases rapidly and the blood aspirin concentration at 2-3 hours must greatly exceed the therapeutic level in order to maintain adequate aspirin concentrations at 8 hours. As a result, efforts have been made to adjust the rate of dissolution and, thus, control the timing of sustained drug release. See, for example, Peters U.S. Pat. No. 3,492,397 where the dissolution rate is said to be controlled by adjusting the wax/ethyl cellulose ratio of the applied spray coating. See also U.S. Pat. Nos. 4,205,060 and 3,488,418 where it is indicated that the rate of dissolution can be controlled by varying the thickness of the coating.

Another method for providing an encapsulated pharmaceutical composition is discussed in published European patent Application No. 77,956, published May 4, 1983. EPO Publication No. 77,956 discloses the use of microcapsules containing a coated core material such as pharmaceutical compounds and foodstuffs. The coating is applied by dispersing the core material into a solution containing ethyl cellulose as the wall-forming material. A phase separation of the ethyl cellulose from the dispersion of core material is carried out by cooling the dispersion. During this cooling, an enteric polymer material is incorporated into the ethyl cellulose coating walls by adding the enteric polymer material with stirring while the ethyl cellulose is still in the "gel" state. The enteric polymer material thus added penetrates, and is dispersed into the coating walls. When the microcapsules are administered, the release of the active compound does not generally occur in the stomach. However, the enteric polymer material is easily dissolved in the intestinal tract, thereby making the microcapsules porous. The porosity of the microcapsules promotes the rapid release of the active compound in the intestinal tract.

A similar approach is found in Japanese Patent Publication No. 12614/81, published Mar. 23, 1981. Japanese Publication No. 12614/81 discloses an enteric protective coating composition which will not readily dissolve in acidic gastic juices, but rapidly (within minutes) dissolves at the pH found in the intestines. The enteric coating is an aqueous dispersion of, for example, hydroxy propyl methyl cellulose phthalate, a gelling agent such as diacetin, and hydroxy propyl methyl cellulose. See, also, Japanese Patent Publication No. 11687/81, published Mar. 16, 1981, which uses hydroxy propyl methyl cellulose phthalate as an enteric coating.

The systems described in the EPO and Japanese publications are essentially "delayed" release mechanisms. There is a delay of medicament release in the stomach, but once the coated medicament reaches the intestines, the release of medication is rapid. There is no sustained release of medication in the intestines.

The need thus remains for a sustained-release system which provides initial therapeutic levels of the drug; delays the delivery of another fraction of the drug to eliminate excess concentrations at 2–3 hours, and then, sustains the release of that delayed fraction to provide adequate drug levels for 8 or more hours.

SUMMARY OF THE INVENTION

The present invention meets that need by providing a dual walled coated medicament having a water-soluble core drug, an inner wall microencapsular control coating and an outer wall enteric coating. By enterically coating microcapsules, the release of core drug into the stomach is greatly impeded and the delivery of the drug is substantially delayed until the coated microcapsules reach the intestine. Delaying the delivery of part of the drug allows for incorporation of uncoated or single walled water-soluble drug into a pharmaceutical preparation to reduce the time required to reach therapeutic levels. The uncoated drug rapidly dissolves in the stomach and quickly enters the blood stream. The single walled drug begins to dissolve in the stomach and enter the blood stream in a controlled manner. In the intestines, the outer wall enteric coating film, membrane, or matrix dissolves or disperses in the intestinal fluid. However, the inner microcapsular control coating does not readily dissolve or disperse in the intestines. Rather, the drug is released in an enhanced controlled fashion through the inner microencapsular control coating, film, membrane, or matrix. Excess drug concentrations are minimized and steady long-term release of the drug is maximized.

The inner wall microencapsular control coating is preferably selected from the group consisting of ethyl cellulose, hydroxy propyl cellulose, and carboxy methyl cellulose. Most preferred is ethyl cellulose. Ethyl cellulose is a common microencapsular coating which will not readily dissolve or disperse in the stomach or intestines, but which permits release of the water-soluble drug through the capsule wall.

The outer wall enteric coating is preferably a microencapsular one such as cellulose acetate phthalate. Cellulose acetate phthalate is also a known coating material. A cellulose acetate phthalate outer wall enteric coating greatly impedes the release of the core drug at pH 1.1 as found in the stomach. But, cellulose acetate phthalate dissolves at pH 7.5 as found in the intestine to allow the release of the drug. Other enteric coatings may be used as long as they do not readily dissolve or disperse in the gastric juices of the stomach but do dissolve or disperse in the intestinal fluid of the intestines. For example, hydroxypropyl methyl cellulose phthalate, polyvinyl acetate phthalate, hydroxyethyl ethyl cellulose phthalate, cellulose acetate tetrahydrophthalate, acrylic resin, shellac, wax, or other film-forming materials which dissolve or disperse in the intestine but remain intact in the stomach are possible alternatives.

The core drug should be one which is reasonably water soluble so as to slowly releasable in the intestines through the inner wall microencapsular control coating. Preferred are aspirin, acetaminophen, dextromethorphan hydrobromide, disopyramide phosphate and furosemide. Other usable water-soluble drugs include various vitamins, minerals, antibiotics, and other analgesics.

The water-soluble drug is preferably microencapsulated in granular form by a coacervation, spray coating or other process prior to having the outer wall enteric coating applied. The phase ratio of to core drug phase to inner wall phase is preferably from approximately 2:1 to 30:1, and more preferably from approximately 2:1 to 20:1. The outer wall enteric coating is also preferably applied by a coacervation, spray coating or other process. The phase ratio of the microencapsulated core drug phase to the enteric coating phase is preferably from approximately 4:1 to 30:1, is more preferably from approximately 4:1 to 12:1 and is most preferably from approximately 4:1 to 8:1. The resulting dual walled coated medicament has highly desirable release kinetics. In this form, the dual walled coated medicament will not release significant amounts of drug in the stomach. However, the outer wall enteric coating will dissolve or disperse in the intestines. Because the inner wall microencapsulated control coating remains, the drug is slowly and steadily released in the intestines.

The dual walled coated medicament may also be admixed with other fractions of free and/or timed-release drug. The admixture may be placed in either capsules or tablets along with other usual ingredients such as binders, fillers, lubricants, etc. In this form free drug is released immediately in the stomach. The dual walled coated medicament does not release drug in the stomach; but rather, in the intestines, drug is released slowly and steadily from the dual walled coated portion of the admixture by reason of the mechanism discussed above. The admixture, thus, provides for both immediate and sustained release of the drug.

The optimum sustained-release pharmaceutical preparation for 8 hour sustained-release aspirin, for example, has been determined to be 400–600 mg. of uncoated aspirin and 400–600 mg. of aspirin in 6:1 phase ratio cellulose acetate phthalate encapsulated 8:1 phase ratio ethyl cellulose microcapsules. A 975 mg. (active ingredient) admixture of this formulation produces a steady blood aspirin concentration versus time curve which rapidly reaches therapeutic levels, does not give excess blood concentration at any time, and maintains therapeutic levels for 8 hours.

Generally, the preferred analgesic therapeutic level of aspirin in the blood stream is between about 20 and 45 mg./l. Additional aspirin levels above 45 mg./l. are believed to have no additional analgesic effect. Further, there is an increased risk of toxicity associated with higher blood levels of aspirin.

Ordinary timed-release aspirin (tableted ethyl cellulose microencapsulated aspirin particles) containing 1300 mg. aspirin maintains therapeutic levels (i.e. above about 20 gm/l) for 8 hours, but gives an aspirin concentration greatly in excess of the therapeutic level 2–3 hours after ingestion of the tablets. Comparatively, the 25% reduction in dosage while maintaining therapeutic aspirin blood concentrations makes the sustained-release pharmaceutical preparation of the present invention therapeutically and/or economically attractive.

1300 mg. of an admixture containing 325-425 mg. of uncoated aspirin and 875-975 mg. aspirin in 6:1 phase ratio cellulose acetate phthalate encapsulated 8:1 phase ratio ethylcellulose microcapsules provides a 12 hour sustained release-aspirin formulation with the peak blood aspirin concentrations considerably lower than the peak blood aspirin concentration for Bayer timed-release aspirin, yet maintains therapeutic blood aspirin concentrations 12 hours after ingestion of the dosage.

Accordingly, it is an object of the present invention to provide a sustained-release pharmaceutical preparation which has desirable release kinetics and yet has a better therapeutic index and/or is more economical to produce. It is another object of the present invention to provide a dual walled coated medicament which may be used either alone or may be combined with other fractions of free and/or timed-release drug as a sustained-release pharmaceutical preparation.

Other objects and advantages of the present invention will be apparent from the following description and the appended claims.

DESCRIPTION OF THE PREFERRED EMBODIMENTS

The preferred dual walled coated medicament of the present invention is a granular aspirin core drug microencapsulated with an ethyl cellulose inner wall microencapsular control coating and a cellulose acetate phthalate outer wall enteric coating. The preferred 8 hour sustained-release pharmaceutical preparation is an admixture of that dual walled coated aspirin and uncoated aspirin particles, with an optimum formulation of 480 mg. uncoated aspirin and 495 mg. of aspirin in 6:1 phase ratio cellulose acetate phthalate encapsulated 12:1 phase ratio ethyl cellulose microcapsules.

The preferred sustained-release pharmaceutical preparation for 12 hour sustained release aspirin is an admixture of 325-425 mg. unencapsulated aspirin and 875-975 mg. of 6:1 phase ratio cellulose acetate phthalate encapsulated 8:1 phase ratio ethyl cellulose microcapsules.

Examples of other water-soluble drugs which may be used as the core drug include most preferably acetaminophen, furosemide, disopyramide phosphate, and dextromethorphan. In addition to these classes of water-soluble drugs others may also be used. For example vitamins, minerals, antibiotics, and other analgesics may be used as the core drug. As long as the drug has sufficient water solubility to be releasable in the intestines through the inner wall microencapsular control coating, is or can be made granular, and is capable of having the dual wall structure of the present invention applied to the granular drug, it is usable.

Other preferred inner wall microencapsular control coatings include hydroxy propyl cellulose and carboxy methyl cellulose. As mentioned, the inner wall microencapsular control coating should be one which does not readily dissolve or disperse in either the stomach or the intestines. It must, however, permit the aqueous intestinal fluids to diffuse through the capsule wall, dissolve the water-soluble core drug, and slowly diffuse or leach out through the capsule wall. It should also be a material which is preferably applicable by coacervation, spray coating or other processes to the granular drug. An ethyl cellulose capsule wall applied in a cyclohexane solution and coacervated by introduction of a phase-separation inducing agent (as taught by U.S. Pat. Nos. 3,155,590; 3,341,416; 3,488,418 and 3,531,418, among others) is most preferred.

Cellulose acetate phthalate is the preferred outer wall enteric coating because it can be applied by coating processes (such as spray coating) or it can be applied by a coacervation process. Cellulose acetate phthalate is also particularly preferred because it will not readily dissolve or disperse at the low pH (around 1.1) of the gastric juices in the stomach. It remains relatively undissolved for over 2 hours under those conditions. And yet, at the higher pH (around 7.5) of the intestinal fluids found in the intestines cellulose acetate phthalate will dissolve or disperse. Other materials which may be used for such purposes are acrylic resin, shellac, wax, and phthalate or polyphthalate esters of film-forming polymers such as those already mentioned.

In a coacervation process cellulose acetate phthalate may be applied to the already encapsulated core drug by adding the ethyl cellulose encapsulated particles to cellulose acetate phthalate dissolved preferably in a buffer with a pH above 5.5, such as a 1% aqueous solution of disodium hydrogen phosphate ($Na_2HPO_4$). A phase separation inducing agent, preferably a 10–40% aqueous solution of a soluble salt such as aqueous sodium sulfate, is used to coacervate the cellulose acetate phthalate and form the outer wall enteric coating. The preferred hardener for the cellulose acetate phthalate outer wall is acetic acid (HOAc); although, other inorganic or low molecular weight organic acids may be used. The type and amount of phase separation inducing agent and hardener is a function of the amount of cellulose acetate phthalate and the pH and strength of the buffer. Thus, the objective is to add a phase separation inducing agent to cause coacervation. Following coacervation the cellulose acetate phthalate encapsulated ethyl cellulose microcapsulate is hardened by reduction of the pH to below about 5.5, preferably to below about 4.0 pH. The dual wall microcapsules may then be washed and dried. The basic coacervation process is similar to the one reported by Merkle and Spieser in J. Pharm. Sci., 62:1444 (1973).

The ratio of the encapsulated core drug phase to the enteric coating phase is preferably from approximately 4:1 to 30:1 and more preferably from approximately 4:1 to 12:1. The phase ratio determines the thickness of the outer wall enteric coating. the phase ratio of the core drug phase to inner wall microencapsular coating phase is preferably from approximately 2:1 to 30:1 and more preferably from approximately 2:1 to 20:1. Table I below illustrates this as well as the degree to which the enteric coating prevents dissolution or dispersion in gastric juices.

TABLE I A

| pH 1.1 HCl/NaCl Buffer 4:1 CELLULOSE ACETATE PHTHALATE PHASE RATIO | | |
|---|---|---|
| ETHYL CELLULOSE PHASE RATIO | ELAPSED TIME | % DISSOLVED |
| 16:1 | 1 hr. | <10% |
| 12:1 | 1 hr. | <10% |
| 8:1 | 1 hr. | <10% |
| 16:1 | 2 hrs. | <10% |
| 12:1 | 2 hrs. | <10% |
| 8:1 | 2 hrs. | <10% |

TABLE I B pH 7.5 phosphate/NaOH buffer
4:1 CELLULOSE ACETATE PHTHALATE PHASE RATIO

| ETHYL CELLULOSE PHASE RATIO | ELAPSED TIME | % DISSOLVED |
|---|---|---|
| 16:1 | 1 hr. | 60% |
| 12:1 | 1 hr. | 25% |
| 8:1 | 1 hr. | 10% |
| 16:1 | 2 hrs. | 75% |
| 12:1 | 2 hrs. | 50% |
| 8:1 | 2 hrs. | 15% |
| 16:1 | 3 hrs. | 90% |
| 12:1 | 3 hrs. | 70% |
| 8:1 | 3 hrs. | 20% |
| 16:1 | 4 hrs. | 95% |
| 12:1 | 4 hrs. | 80% |
| 8:1 | 4 hrs. | 25% |

The dissolution studies set forth in Table I were with a dual walled coated aspirin having an ethyl cellulose inner wall and a cellulose acetate phthalate outer wall. The tests were performed using the USP XX basket method. In each run a 750 mg. sample was placed in the basket rotated at 50 RPM in a 1 liter, 3-neck round bottom flask containing a buffer as set forth in Table I A at 37° C. After 2 hours the basket was removed from the flask, placed in a second flask containing a buffer as set forth in Table I B and rotated at 50 RPM for another 4 hours.

The buffer of Table I A is at the pH of gastric juices and the buffer of Table I B is at the pH of intestinal fluid. The dissolution procedure may also be performed using simulated digestive fluids. The composition of the buffers and digestive fluids is described in USP XX. In this instance simulated gastric juice is substituted for pH 1.1 buffer and simulated intestinal fluid is substituted for pH 7.5 buffer. Use of the digestive fluids is preferred if enzymes affect dissolution and is necessary if the coating contains lipid polymers or other enzymatically-degradable materials. However, neither of these conditions exists in the dissolution tests of Table I above (or Table II below) and performing the dissolutions in simulated digestive fluids does not significantly affect the dissolution rates of the dual walled coated medicament of the present invention.

The same basket dissolution method used in Table I was used for the tests of Table II below. Those runs were made with (A) Bayer timed-release aspirin, (B) 16:1 phase ratio ethyl cellulose microencapsulated aspirin capsules, and (C) dual walled coated aspirin having an inner wall of 12:1 phase ratio ethyl cellulose and an outer wall of 4:1 phase ratio cellulose acetate phthalate.

TABLE II A

| | pH 1.1 HCl/NaCl buffer | |
|---|---|---|
| RUN | ELAPSED TIME | % DISSOLVED |
| A | 1 hr. | 40% |
| B | 1 hr. | 20% |
| C | 1 hr. | <10% |
| A | 2 hrs. | 60% |
| B | 2 hrs. | 35% |
| C | 2 hrs. | <10% |

TABLE II B

| | pH 7.5 Phosphate/NaOH buffer | |
|---|---|---|
| RUN | ELAPSED TIME | % DISSOLVED |
| A | 1 hr. | 90% |
| B | 1 hr. | 65% |
| C | 1 hr. | 30% |
| A | 2 hrs. | 100% |
| B | 2 hrs. | 80% |
| C | 2 hrs. | 50% |
| A | 3 hrs. | 100% |
| B | 3 hrs. | 85% |
| C | 3 hrs. | 65% |
| A | 4 hrs. | 100% |
| B | 4 hrs. | 90% |
| C | 4 hrs. | 85% |

Table II shows that the dual walled coated medicament of the present invention (run C) effectively delays dissolution (and drug release) until the basket is placed in pH 7.5 buffer and even then, the dissolution of run C is slow and steady. On the other hand, runs A and B rapidly released aspirin at pH 1.1 and were nearly completely dissolved shortly after introduction into the pH 7.5 buffer. Again, performing the dissolution studies in simulated digestive fluids does not significantly effect the dissolution rates of any of runs A, B or C. The preferred dual walled coated medicament and sustained-release pharmaceutical preparations may be prepared as best illustrated in the following examples.

EXAMPLE 1

A twelve hour sustained-release pharmaceutical preparation utilizing the dual wall coating of the present invention was prepared as follows.

14.25 gr. ethyl cellulose, 48–49.5% ethoxylated, viscosity 100 (Dow Ethocel Premium) and 9.5 gr. polyethylene (Kodak Epolene C-10) were added to 600 ml of cyclohexane. The mixture was refluxed for 20 minutes with stirring to form a solution. 114 gr. of aspirin, USP No. 40 crystals (Dow), were added to the solution and the mixture was cooled to 20° C. in 20 minutes. The mixture was filtered and the filter cake was washed with 500 ml cyclohexane. The resulting aspirin ethyl cellulose microcapsules were dried by sieving through a 20 mesh screen 3 times.

72 gr. of the aspirin ethyl cellulose microcapsules were added to a stirred solution of 12 gr. cellulose acetate phthalate (Eastman C.A.P.) and 4.5 gr. $Na_2HPO_4$ in 585 gr. water at 40° C. While stirring, 420 gr. of 30% aqueous sodium sulfate were added dropwise over a 4.5 minute period. The outer wall enteric coating was fixed by the immediate addition of 90 ml of 20% acetic acid. The resulting dual walled microcapsules were filtered, washed with 750 ml of 2% acetic acid and dried for 20 minutes in a fluidized bed drier at 25° C. The aspirin content was found to be 77.4%. The above described procedure produced 6:1 phase ratio cellulose acetate phthalate encapsulated 8:1 phase ratio ethyl cellulose aspirin capsules. The phase ratio is determined by the amounts of polymer and drug used in preparation of the microcapsules. Thus 114 gr. of aspirin encapsulated with 14.25 gr. of ethyl cellulose inner wall material equals a phase ratio of 114 to 14.25 or 8 to 1. Likewise 72 gr. of aspirin ethyl cellulose microcapsules encapsulated with 12 gr. of cellulose acetate phthalate equals a phase ratio of 72 to 12 or 6 to 1.

38.00 grams of the dual walled microcapsule aspirin were mixed with 11.92 gr. USP aspirin powder (J. J. Baker). Size 00 gelatin capsules were filled with the mixture to contain 433 mg. aspirin, 125 mg. of which was free aspirin and 308 mg. of which was dual wall encapsulated aspirin. Clinical trials were performed with two capsules of the aspirin compound of the instant invention. The two capsules together contained 867 mg. of aspirin (250 mg. free aspirin and 617 mg. of dual wall encapsulated aspirin). The trials were conducted against 1300 mg. Bayer Timed Release aspirin in a six subject cross-over study. As can be seen from the data in Tables IIIA and IIIB, the formulation containing dual walled microcapsules and free aspirin provided nearly constant blood salicylate concentrations.

TABLE III A 867 mg. uncoated aspirin/dual wall coated aspirin mix

| ELAPSED TIME | BLOOD ASA CONCENTRATION (mg./l.) |
|---|---|
| 1 hr. | 18 |
| 2 hrs. | 19 |
| 3 hrs. | 21 |
| 4 hrs. | 21 |
| 5 hrs. | 19 |
| 6 hrs. | 21 |
| 7 hrs. | 19 |
| 8 hrs. | 17 |
| 9 hrs. | 16 |
| 10 hrs. | 15 |
| 11 hrs. | 15 |
| 12 hrs. | 15 |
| 13 hrs. | 14 |
| 14 hrs. | 13 |
| 15 hrs. | 12 |
| 16 hrs. | 11 |

TABLE III B 1300 mg. Bayer, ethyl cellulose coated time release aspirin

| ELAPSED TIME | BLOOD ASA CONCENTRATION (mg./l.) |
|---|---|
| 1 hr. | 34 |
| 2 hrs. | 57 |
| 3 hrs. | 68 |
| 4 hrs. | 80 |
| 5 hrs. | 86 |
| 6 hrs. | 77 |
| 7 hrs. | 67 |
| 8 hrs. | 57 |
| 9 hrs. | 54 |
| 10 hrs. | 51 |
| 11 hrs. | 46 |
| 12 hrs. | 41 |
| 13 hrs. | 37 |
| 14 hrs. | 32 |
| 15 hrs. | 28 |
| 16 hrs. | 24 |

The Bayer Timed-Release aspirin provided wide variations in blood salicylate concentrations, gave a high peak concentration and saturated the body's salicylate elimination mechanism to maintain high salicylate concentrations.

EXAMPLE 2

25.00 gr. of the dual-walled microcapsules from Example 1 were mixed with 18.76 gr. of powdered aspirin. Gelatin capsules were filled with 375 mg. of the mixture to contain 325 mg. aspirin, 160 g. of which was free aspirin, and 165 g. of which was dual wall microencapsulated aspirin of the present invention. Clinical trials were performed with 975 mg. of aspirin (three, 375 mg. capsules, together containing 480 mg. free aspirin and 495 mg. of dual wall microencapsulated aspirin) in the capsules and 975 mg. Bayer Regular Aspirin. As can be seen in TABLES IV-A and IV-B the sustained-release formulation gave more constant blood salicylate concentrations than plain aspirin with peak blood levels half of that produced by free aspirin.

TABLE IV A 975 mg. uncoated aspirin/dual walled coated aspirin mix

| ELAPSED TIME | BLOOD ASA CONCENTRATION (mg./l.) |
|---|---|
| 1 hr. | 30 |
| 2 hrs. | 34 |
| 3 hrs. | 34 |
| 4 hrs. | 31 |
| 5 hrs. | 29 |
| 6 hrs. | 25 |
| 8 hrs. | 18 |
| 10 hrs. | 14 |
| 12 hrs. | 13 |

TABLE IV B 975 mg. Regular Bayer Aspirin

| ELAPSED TIME | BLOOD ASA CONCENTRATION (mg./l.) |
|---|---|
| 1 hr. | 63 |
| 2 hrs. | 68 |
| 3 hrs. | 62 |
| 4 hrs. | 56 |
| 5 hrs. | 51 |
| 6 hrs. | 42 |
| 8 hrs. | 26 |
| 10 hrs. | 16 |
| 12 hrs. | 7 |

EXAMPLE 3

A solution was formed with 200 ml water, 30 ml. polyethylene glycol 400, 2 gr. $Na_2HPO_4$ and 4 gr. polyvinyl acetate phthalate (Canada Packers). The pH was adjusted to 4.85 with 0.1N HCl. 16 gr. of 8:1 phase ratio aspirin ethyl cellulose microcapsules prepared in the procedure in Example I were added to the solution at 55° C. 200 gr. of 30% aqueous sodium sulfate were added over a 4 minute period.

A silica dispersion was then prepared in the following manner. A mixture of 2 gr. aerosil R972 hydrophobic silica powder (Degussa, Teterboro, NJ) and 10 drops, 2% Naccanol in water (Stepan, Northfield, Ill.) was dispersed in 300 ml water and the pH was lowered to 3.0 with 0.1N HCl. This silica dispersion (at 25° C.) was added to the mixture containing the microcapsules. The pH was further reduced to 2.75 and the mixture was cooled to 25° C. The microcapsules were filtered, washed with 500 ml water acidified to pH 2.75 with 0.1N HCl, and dried in a fluidized bed drier.

The same basket dissolution method used in conjunction with the data set forth in Tables I-A and I-B was used to test the polyvinyl acetate phthalate coated capsules produced in this example. The data from the tests of the polyvinyl acetate phthalate coated capsules is set forth in Tables V-A and V-B. Table V-A shows that the polyvinyl acetate phthalate outer wall effectively precludes dissolution (and drug release) in the pH 1.1 buffer. As discussed above, the pH 1.1 buffer simulates conditions in the stomach.

TABLE V-A pH 1.1 HCl/NaCl BUFFER
POLYVINYL ACETATE PHTHALATE
OUTER MICROENCAPSULAR WALL

| ELAPSED TIME | % DISSOLVED |
|---|---|
| 1 hr. | 1 |

TABLE V-A-continued pH 1.1 HCl/NaCl BUFFER
POLYVINYL ACETATE PHTHALATE
OUTER MICROENCAPSULAR WALL

| ELAPSED TIME | % DISSOLVED |
|---|---|
| 2 hrs. | 2 |

TABLE V B pH 7.5 PHOSPHATE BUFFER
POLYVINYL ACETATE PHTHALATE
OUTER MICROENCAPSULAR WALL

| ELAPSED TIME | % DISSOLVED |
|---|---|
| 1 hr. | 26 |
| 2 hrs. | 44 |
| 4 hrs. | 68 |

EXAMPLE 4

2:1 phase ratio furosemide-ethyl cellulose microcapsules were prepared by the phase separation of ethyl cellulose from cyclohexane containing polyethylene. A second microencapsular wall of cellulose acetate phthalate was applied by the coacervation method described in Example 1.

The same basket dissolution method used to produce the data set forth in Tables I-A and I-B was used for the tests reported in Tables VI-A and VI-B below. Table VI-A shows that the dual-walled microcapsules do not release any substantial amount of furosemide in pH 1.1 buffer. Table VI-B shows that a slow dissolution of the drug is achieved in pH 7.5 buffer.

TABLE VI A pH 1.1 HCl/NaCl BUFFER
FUROSEMIDE DUAL-WALLED
MICROENCAPSULAR DRUG

| ELAPSED TIME | % DISSOLVED |
|---|---|
| 1 hr. | <1 |
| 2 hrs. | <1 |

TABLE VI B pH 7.5 BUFFER
FUROSEMIDE DUAL-WALLED
MICROENCAPSULAR DRUG

| ELAPSED TIME | % DISSOLVED |
|---|---|
| 1 hr. | 47 |
| 2 hrs. | 62 |
| 4 hrs. | 76 |
| 6 hrs. | 82 |

Tables VII-A shows computer predicted blood furosemide concentration versus time curve for 80 mg. free furosemide. Table VII-B shows a computer predicted blood concentration versus time curve for a sustained release formulation composed of 20 mg. free furosemide and 60 mg. of furosemide in the dual walled microcapsules of Example IV. Free furosemide reaches a high peak concentration after 1 hour then rapidly declines. The sustained-release formulation maintains a generally consistent blood furosemide concentration.

TABLE VII A 80 mg. Free Furosemide
PREDICTED BLOOD FUROSEMIDE CONCENTRATION

| ELAPSED TIME | FUROSEMIDE CONCENTRATION |
|---|---|
| 1 hr. | 2.2 mg./l. |
| 2 hrs. | 1.3 mg./l. |
| 3 hrs. | 0.6 mg./l. |
| 4 hrs. | 0.3 mg./l. |
| 6 hrs. | 0.1 mg./l. |
| 8 hrs. | 0.1 mg./l. |

TABLE VII B 80 mg. Sustained Release
PREDICTED BLOOD FUROSEMIDE CONCENTRATION

| ELAPSED TIME | FUROSEMIDE CONCENTRATION |
|---|---|
| 1 hr. | 0.6 mg./l. |
| 2 hrs. | 0.4 mg./l. |
| 3 hrs. | 0.7 mg./l. |
| 4 hrs. | 0.8 mg./l. |
| 6 hrs. | 0.4 mg./l. |
| 8 hrs. | 0.2 mg./l. |

EXAMPLE 5

Capsules of 40 mesh ethyl cellulose encapsulated aspirin were prepared by the coacervation process described in U.S. Pat. No. 3,155,590. 8.0 grams of capsules were added to 100 grams of a 2% solution of cellulose acetate phthalate in a 1% aqueous solution of KNaHPO$_4$ and stirred at 55° C. While stirring 20 ml. of 20% aqueous sodium sulfate solution was added to the system in 30 seconds. This was immediately followed by the dropwise addition of 40 ml. of 20% aqueous sodium sulfate in 4.5 minutes. Coacervation resulted in coating of the ethyl cellulose encapsulated aspirin capsules with an outer wall of cellulose acetate phthalate at a phase ratio of 4:1. The outer walled enteric coating was fixed by the addition of 5 ml of 14% HOAc in 1 minute. The resulting dual walled coated capsules were washed with 2% HOAc and dried for 1 hour on a 60 mesh screen in a fluidized bed drier.

Studies were undertaken to determine the optimum formulation for an 8-hour sustained-release pharmaceutical preparation utilizing the dual walled coated aspirin of this example. It was determined that preferred is 480 mg. uncoated aspirin and 495 mg. of aspirin in the 4:1 phase ratio cellulose acetate phthalate encapsulated 8:1 phase ratio ethyl cellulose aspirin capsules. The optimum formulation was determined by choosing the combination which had the blood curve with the best least-square curve fit to a constant 30 mg/liter blood concentration.

The predicted blood curve for the optimum formulation is set forth in Table VIII below.

TABLE VIII 975 mg. uncoated aspirin/dual walled coated aspirin mix

| ELAPSED TIME | BLOOD ASA CONCENTRATION (mg./l.) |
|---|---|
| 1 hr. | 25 |
| 2 hrs. | 29 |
| 3 hrs. | 30 |
| 4 hrs. | 34 |
| 5 hrs. | 33 |
| 6 hrs. | 33 |
| 7 hrs. | 25 |
| 8 hrs. | 20 |

EXAMPLE 6

This example illustrates the formation of the dual-walled microcapsules of this invention by a spray coating technique.

800 gm of a granulated aspirin (Asagran 1640, Monsanto) was placed in the Wurster bowl of a Uniglatt fluid bed spray coating machine. The inner microencapsular wall was applied by spraying onto the aspirin a dispersion of 200 gm Aquacoat aqueous ethylcellulose dispersion (FMC Corporation), 14.4 gm Myvacet 9-40 acetylated monoglycerides (Eastman Chemical Products) and water to dilute the solids content to 20% of the weight of the dispersion. 221 gm of the dispersion was sprayed onto the aspirin to yield microcapsules with a phase ratio of 19:1.

The outer microencapsular wall was also applied by spray coating. The second coating dispersion was prepared by adding to 218 gm of water, slowly stirred, in a blender, 12 gm of Talc (2755 Lo-micron Talc USP, Whittaker), 0.75 gm antifoam agent (Medical Antifoam AF Emulsion, Dow Corning) and a solution of 10 gm polyethylene glycol 8000 (Baker) and 2 gm polyethylene glycol 1000 (Baker) in 108 gm water. The blender was then run at high speed for 1 minute. This suspension was poured into 120 gm of Eudragit L 30 D aqueous acrylic resin dispersion (Rohm Pharma). 209 gm of this dispersion was sprayed onto 600 gm of ethylcellulose encapsulated aspirin to yield dual walled microcapsules with an ethylene aspirin microcapsule to enteric coating phase ratio of 19:1.

The same basket dissolution method used in conjunction with the data set forth in Tables I-A and I-B was used to test the dual walled microcapsules prepared in this example. The data from the tests of dual walled microcapsules prepared in this example. The data from the tests of dual walled microcapsules prepared by spray coating is set forth in Tables IX-A and IX-B. Table IX-A shows that the outer wall effectively precludes dissolution (and drug release) in the pH 1.1 buffer. As discussed above, the pH 1.1 buffer simulates conditions in the stomach. Table IX-B shows that the aspirin is released in a controlled manner in the pH 7.5 buffer which simulates conditions in the intestine.

TABLE IX-A

| pH 1.1 HCl/NaCl Buffer Dual Walled Microcapsules Prepared by Spray Coating | |
|---|---|
| ELAPSED TIME | % DISSOLVED |
| 1 hr. | <5 |
| 2 hrs. | <5 |

TABLE IX-B

| pH 7.5 Phosphate Buffer Dual Walled Microcapsules Prepared by Spray Coating | |
|---|---|
| ELAPSED TIME | % DISSOLVED |
| 1 hr. | 23 |
| 2 hrs. | 35 |
| 4 hrs. | 52 |

While the product and method herein described constitute preferred embodiments of the invention, it is to be understood that the invention is not limited to this precise product and method, and that changes may be made therein without departing from the scope of the invention.

What is claimed is:

1. A sustained-release pharmaceutical preparation comprising microcapsules of a dual walled coated medicament having a core, an inner wall microencapsular control coating, and an outer wall enteric coating wherein:

said core is a water-soluble drug capable of being absorbed from the stomach and the intestines, and has sufficient water solubility to be slowly releasable in the intestines through said inner wall microencapsular control coating, said core being in granular form, said inner wall microencapsular control coating is on said granular core drug, said microencapsular control coating being one which will not dissolve or disperse readily in the intestines, but which permits aqueous intestinal fluids to diffuse therethrough, dissolve said water-soluble core drug, and slowly diffuse or leach out therethrough, whereby in the intestines said drug is slowly released through said microencapsular control coating to maintain therapeutic levels of said drug, and said outer wall enteric coating is over said inner wall microencapsular control coating, said outer wall enteric coating being one which will not dissolve or disperse readily in the stomach but which dissolves or disperses in the intestines, whereby said dual walled coated medicament will release less than 10% per hour of said drug while in the stomach, but will slowly release said drug in the intestines to provide adequate drug levels for 8 or more hours without resulting in excess drug levels at anytime.

2. The sustained release pharmaceutical preparation of claim 1 wherein said inner wall microencapsular control coating is coated on said granular core drug at a phase rate of drug to microencapsular control coating of from approximately 2:1 to 20:1 to form an inner wall coated drug, and said outer wall enteric coating is coated on said inner wall coated drug at a phase ratio of inner wall coated drug to outer wall enteric coating of from approximately 4:1 to 12:1.

3. The sustained-release pharmaceutical preparation of claim 2 wherein said inner wall microencapsular control coating is selected form the group consisting of ethyl cellulose, hydroxy propyl cellulose, carboxy methyl cellulose, and admixtures thereof.

4. The sustained-release pharmaceutical preparation of claim 3 wherein said outer wall enteric coating is selected form the group consisting of cellulose acetate phthalate, hydroxypropyl methyl cellulose phthalate, polyvinyl acetate phthalate, hydroxyethyl ethyl cellulose phthalate, cellulose acetate tetrahydrophthalate, acrylic resin, shellac and wax.

5. The sustained-release pharmaceutical preparation of claim 4 wherein said drug is selected from the group consisting of aspirin, acetaminophen, dextromethorphan hydrobromide, disopyramide phosphate and furosemide.

6. The sustained-release pharmaceutical preparation of claim 5 wherein said drug is granular aspirin, said inner wall microencapsular control coating is ethyl cellulose, and said outer wall enteric coating is cellulose acetate phthalate.

* * * * *